(12) United States Patent
Zhang et al.

(10) Patent No.: US 10,755,410 B2
(45) Date of Patent: Aug. 25, 2020

(54) METHOD AND APPARATUS FOR ACQUIRING INFORMATION

(71) Applicant: BAIDU ONLINE NETWORK TECHNOLOGY (BEIJING) CO., LTD., Beijing (CN)

(72) Inventors: Shaoting Zhang, Beijing (CN); Weidong Zhang, Beijing (CN); Qi Duan, Beijing (CN)

(73) Assignee: BAIDU ONLINE NETWORK TECHNOLOGY (BEIJING) CO., LTD., Beijing (CN)

( * ) Notice: Subject to any disclaimer, the term of this patent is extended or adjusted under 35 U.S.C. 154(b) by 70 days.

(21) Appl. No.: 16/051,179

(22) Filed: Jul. 31, 2018

(65) Prior Publication Data

US 2019/0102879 A1 Apr. 4, 2019

(30) Foreign Application Priority Data

Sep. 30, 2017 (CN) .......................... 2017 1 0919995

(51) Int. Cl.
*G06T 7/00* (2017.01)
*G06K 9/00* (2006.01)
(Continued)

(52) U.S. Cl.
CPC .............. *G06T 7/0012* (2013.01); *A61B 3/00* (2013.01); *A61B 3/12* (2013.01); *G06K 9/0061* (2013.01);
(Continued)

(58) Field of Classification Search
CPC .... G16H 20/10; G06K 9/6262; G06K 9/6269; G06K 9/186; G06T 7/0012; G06N 7/005; G06N 5/022; A61B 5/0062; G06F 19/10
(Continued)

(56) References Cited

U.S. PATENT DOCUMENTS 8,737,703 B2 5/2014 Mangoubi et al.
2004/0015459 A1 1/2004 Jaeger
(Continued)

FOREIGN PATENT DOCUMENTS

| CN | 103858134 A | 6/2014 |
| CN | 106530295 A | 3/2017 |
| CN | 107203778 A | 9/2017 |

OTHER PUBLICATIONS

Gulshan et al., "Development and Validation of a Deep Learning Algorithm for Detection of Diabetic Retinopathy in Retinal Fundus Photographs", JAMA, Original Investigation, Innovations in Health Care Delivery, 316: 2366-2368 (2016).
(Continued)

*Primary Examiner* — Phuoc H Doan
(74) *Attorney, Agent, or Firm* — Marshall, Gerstein & Borun LLP (57) ABSTRACT

The present disclosure discloses a method and apparatus for acquiring information. An implementation of the method comprises: acquiring a fundus image; introducing the fundus image into a pre-trained pathological classification model to obtain pathological classification information, wherein the pathological classification model is used for characterizing correspondence between a pathological area image contained from the fundus image and the pathological classification information, and the pathological classification information comprises at least one of diabetic retinopathy classification information and diabetic macular edema classification information; and establishing output information based on the pathological classification information. This implementation concurrently acquires diabetic retinopathy classification information and diabetic macular edema classification information from the fundus image, and may make full use of the correlation between diabetic retinopathy and diabetic macular edema in diagnosis to effectively improve (Continued)

the accuracy of diabetic retinopathy classification and diabetic macular edema classification in the process of computer aided diagnosis.

13 Claims, 5 Drawing Sheets

(51) Int. Cl.
| | | |
|---|---|---|
| *G06T 7/11* | (2017.01) | |
| *G06N 5/04* | (2006.01) | |
| *G06N 3/08* | (2006.01) | |
| *G06T 7/187* | (2017.01) | |
| *G06N 3/04* | (2006.01) | |
| *A61B 3/00* | (2006.01) | |
| *A61B 3/12* | (2006.01) | |
| *G06N 20/10* | (2019.01) | |
| *G06N 7/00* | (2006.01) | |
| *G06K 9/46* | (2006.01) | |

(52) U.S. Cl.
CPC ....... *G06K 9/00617* (2013.01); *G06N 3/0454* (2013.01); *G06N 3/08* (2013.01); *G06N 5/046* (2013.01); *G06T 7/11* (2017.01); *G06T 7/187* (2017.01); *G06K 9/4628* (2013.01); *G06N 3/0436* (2013.01); *G06N 7/005* (2013.01); *G06N 20/10* (2019.01); *G06T 2207/20084* (2013.01); *G06T 2207/30041* (2013.01)

(58) Field of Classification Search
USPC ............ 382/128, 139, 161; 705/44; 235/380
See application file for complete search history.

(56) References Cited

U.S. PATENT DOCUMENTS

2017/0372117 A1* 12/2017 Bredno ................ G06K 9/0014
2018/0214087 A1* 8/2018 Balaji .................. A61B 5/7264

OTHER PUBLICATIONS

Zheng et al., "Automatic Analysis Method of Macular Edema Classification for Diabetic Retinopathy Images", Chinese Journal of Biomedical Engineering. 33: 687-695 (2014).

* cited by examiner

METHOD AND APPARATUS FOR ACQUIRING INFORMATION

CROSS-REFERENCE TO RELATED APPLICATION

This application claims priority to Chinese Application No. 201710919995.5, filed with the State Intellectual Property Office of the People's Republic of China (SIPO) on Sep. 30, 2017, the content of which is incorporated herein by reference in its entirety.

TECHNICAL FIELD

The embodiments of the present disclosure relate to the field of data processing technology, specifically to the field of image processing technology, and more specifically to a method and apparatus for acquiring information.

BACKGROUND

Diabetic retinopathy (DR) and diabetic macular edema (DME) are two common diabetic eye diseases (hereinafter referred to as diabetic retinopathies). Diabetic retinopathies are diagnosed mainly based on medical examination of patients' fundus images. The fundus images are analyzed based on DR and DME classification standards to comprehensively evaluate disease conditions and determine therapeutic solutions.

At present, the existing automatic classification and analysis methods of diabetic retinopathies fail to concurrently provide DR and DME classification results.

SUMMARY

An object of an embodiment of the present disclosure is to provide a method and apparatus for acquiring information, to solve the technical problems mentioned in the background part.

In a first aspect, an embodiment of the present disclosure provides a method for acquiring information. The method comprises: acquiring a fundus image; introducing the fundus image into a pre-trained pathological classification model to obtain pathological classification information, wherein the pathological classification model is used for characterizing correspondence between a pathological area image contained from the fundus image and the pathological classification information, and the pathological classification information comprises at least one of diabetic retinopathy classification information and diabetic macular edema classification information; and establishing output information based on the pathological classification information.

In some embodiments, the method further comprises establishing a pathological classification model, and the establishing a pathological classification model comprises retrieving an annotated fundus image from a fundus image database, wherein the annotated fundus image comprises a diabetic retinopathy area image and a diabetic macular edema area image, as well as the diabetic retinopathy classification information and the diabetic macular edema classification information; determining a first information block, and a second information block corresponding to the first information block from the annotated fundus image to obtain a first information block set and a second information block set corresponding to the fundus image database, wherein the first information block is used for characterizing correspondence between the diabetic retinopathy area image and the diabetic retinopathy classification information, and the second information block is used for characterizing correspondence between the diabetic macular edema area image and the diabetic macular edema classification information; and obtaining a pathological classification model by training, using a machine learning method based on the first information block set and the second information block set.

In some embodiments, the obtaining a pathological classification model by training, using a machine learning method based on the first information block set and the second information block set comprises: introducing the first information block and the second information block set corresponding to the first information block into a neural network to obtain a first feedback parameter corresponding to the first information block and a second feedback parameter corresponding to the second information block, wherein the first feedback parameter is used for characterizing the accuracy in acquiring the diabetic retinopathy classification information by the neural network, and the second feedback parameter is used for characterizing the accuracy in acquiring the diabetic macular edema classification information by the neural network; and correcting network parameters of the neural network based on the first feedback parameter and the second feedback parameter, and using the neural network with the corrected network parameters as the pathological classification model.

In some embodiments, the neural network comprises: a convolutional layer and a fully connected layer, wherein the convolutional layer is used for processing the fundus image, and extracting characteristic information existing in a diabetic retinopathy area and a diabetic macular edema area of the fundus image, and the fully connected layer is used for respectively establishing first correspondence between image processing results of the diabetic retinopathy focus area and the diabetic retinopathy classification information, and establishing second correspondence between image processing results of the diabetic macular edema focus area and the diabetic macular edema classification information.

In some embodiments, the correcting network parameters of the neural network based on the first feedback parameter and the second feedback parameter comprises: correcting network parameters of at least one of the convolutional layer and the fully connected layer based on the first feedback parameter and the second feedback parameter.

In some embodiments, the neural network comprises: a first hierarchical network and a second hierarchical network, wherein the first hierarchical network is used for establishing correspondence between the diabetic retinopathy focus area and the diabetic retinopathy classification information, and the second hierarchical network is used for establishing correspondence between the diabetic macular edema focus area and the diabetic macular edema classification information.

In some embodiments, the correcting network parameters of the neural network based on the first feedback parameter and the second feedback parameter comprises: correcting network parameters of the second hierarchical network based on the first feedback parameter, and correcting network parameters of the first hierarchical network based on the second feedback parameter.

In a second aspect, an embodiment of the present disclosure provides an apparatus for acquiring information. The apparatus comprises: a fundus image acquisition unit for acquiring a fundus image; a pathological classification information acquisition unit for introducing the fundus image into a pre-trained pathological classification model to obtain pathological classification information, wherein the pathological classification model is used for characterizing correspondence between a pathological area image contained from the fundus image and the pathological classification information, and the pathological classification information comprises at least one of diabetic retinopathy classification information and diabetic macular edema classification information; and the output information establishing unit for establishing output information based on the pathological classification information.

In some embodiments, the apparatus further comprises a pathological classification model establishing unit for establishing a pathological classification model, wherein the pathological classification model establishing unit comprises an annotated fundus image retrieval subunit, for retrieving an annotated fundus image from a fundus image database, wherein the annotated fundus image comprises a diabetic retinopathy area image and a diabetic macular edema area image, as well as the diabetic retinopathy classification information and the diabetic macular edema classification information; an information block set acquisition subunit, for determining a first information block, and a second information block corresponding to the first information block from the annotated fundus image to obtain a first information block set and a second information block set corresponding to the fundus image database, wherein the first information block is used for characterizing correspondence between the diabetic retinopathy area image and the diabetic retinopathy classification information, and the second information block is used for characterizing correspondence between the diabetic macular edema area image and the diabetic macular edema classification information; and a pathological classification model training subunit, for obtaining a pathological classification model by training, using a machine learning method based on the first information block set and the second information block set.

In some embodiments, the pathological classification model training subunit comprises: a feedback parameter acquisition module, for introducing the first information block and the second information block set corresponding to the first information block into a neural network to obtain a first feedback parameter corresponding to the first information block and a second feedback parameter corresponding to the second information block, wherein the first feedback parameter is used for characterizing the accuracy in acquiring the diabetic retinopathy classification information by the neural network, and the second feedback parameter is used for characterizing the accuracy in acquiring the diabetic macular edema classification information by the neural network; and a pathological classification model acquisition module, for correcting network parameters of the neural network based on the first feedback parameter and the second feedback parameter, and using the neural network with the corrected network parameters as the pathological classification model.

In some embodiments, the neural network comprises: a convolutional layer and a fully connected layer, wherein the convolutional layer is used for processing the fundus image, and extracting characteristic information existing in a diabetic retinopathy area and a diabetic macular edema area of the fundus image, and the fully connected layer is used for respectively establishing first correspondence between image processing results of the diabetic retinopathy focus area and the diabetic retinopathy classification information, and establishing second correspondence between image processing results of the diabetic macular edema focus area and the diabetic macular edema classification information.

In some embodiments, the pathological classification model acquisition module comprises: correcting network parameters of at least one of the convolutional layer and the fully connected layer based on the first feedback parameter and the second feedback parameter.

In some embodiments, the neural network comprises: a first hierarchical network and a second hierarchical network, wherein the first hierarchical network is used for establishing correspondence between the diabetic retinopathy focus area and the diabetic retinopathy classification information, and the second hierarchical network is used for establishing correspondence between the diabetic macular edema focus area and the diabetic macular edema classification information.

In some embodiments, the pathological classification model acquisition module comprises: correcting network parameters of the second hierarchical network based on the first feedback parameter, and correcting network parameters of the first hierarchical network based on the second feedback parameter.

In a third aspect, an embodiment of the present disclosure provides a server, comprising: one or more processors; a memory, for storing one or more programs, wherein the one or more programs enable, when executed by the one or more processors, the one or more processors to execute the method for acquiring information according to the first aspect.

In a fourth aspect, an embodiment of the present disclosure provides a computer readable storage medium, storing a computer program therein, wherein the program implements, when executed by a processor, the method for acquiring information according to the first aspect.

The method and apparatus for acquiring information provided in the embodiments of the present disclosure can concurrently acquire diabetic retinopathy classification information and diabetic macular edema classification information from the fundus image, and may make full use of the correlation between diabetic retinopathy and diabetic macular edema in diagnosis to effectively improve the accuracy of diabetic retinopathy classification and diabetic macular edema classification in the process of computer aided diagnosis.

BRIEF DESCRIPTION OF THE DRAWINGS

By reading and referring to detailed description on the non-limiting embodiments in the following accompanying drawings, other features, objects and advantages of the present disclosure will become more apparent.

DETAILED DESCRIPTION OF EMBODIMENTS

The present disclosure will be further described below in detail in combination with the accompanying drawings and the embodiments. It should be appreciated that the specific embodiments described herein are merely used for explaining the relevant disclosure, rather than limiting the present disclosure. In addition, it should be noted that, for the ease of description, only the parts related to the relevant disclosure are shown in the accompanying drawings.

It should also be noted that the embodiments in the present disclosure and the features in the embodiments may be combined with each other on a non-conflict basis. The present disclosure will be described below in detail with reference to the accompanying drawings and in combination with the embodiments.

Figure 1:
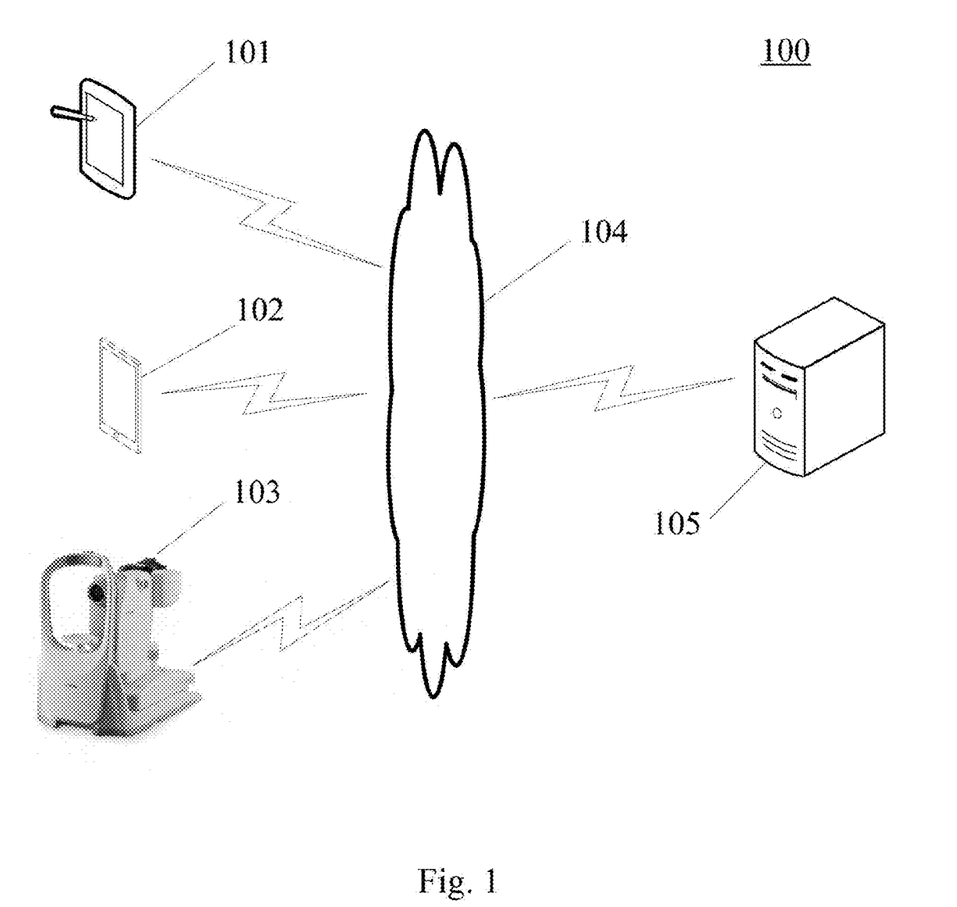
FIG. 1 is an architectural diagram of an exemplary system in which the present disclosure may be applied.

FIG. 1 shows an exemplary architecture of a system 100 which may be used by a method or apparatus for acquiring information according to the embodiments of the present disclosure.

As shown in FIG. 1, the system architecture 100 may include terminal devices 101, 102 and 103, a network 104 and a server 105. The network 104 serves as a medium providing a communication line between the terminal devices 101, 102 and 103 and the server 105. The network 104 may include various types of connections, such as wired or wireless transmission links, or optical fibers.

The user may use the terminal devices 101, 102 and 103 to interact with the server 105 through the network 104, in order to transmit or receive messages, etc. Various image applications, such as fundus image acquisition applications, images editing applications, and information transmitting applications may be installed on the terminal devices 101, 102 and 103.

The terminal devices 101, 102 and 103 may be a variety of electronic devices having display screens and supporting image display, including but not limited to smartphones, tablet computers, laptops, desktop computers, digital fundus cameras, and the like.

The server 105 may be a server that provides a variety of services, such as a server performing image processing on fundus images sent from the terminal devices 101, 102 and 103 to obtain diabetic classification information. The server may analyze the received fundus image data and the like to obtain the diabetic retinopathy classification information and the diabetic macular edema classification information of a corresponding fundus image.

It should be noted that the method for acquiring information provided in an embodiment of the present disclosure is generally executed by the server 105. Accordingly, the apparatus for acquiring information is generally set in the server 105.

It should be understood that the number of the terminal devices, networks and servers in FIG. 1 are only illustrative. There may be any number of terminal devices, networks, and servers based on implementation needs.

Figure 2:
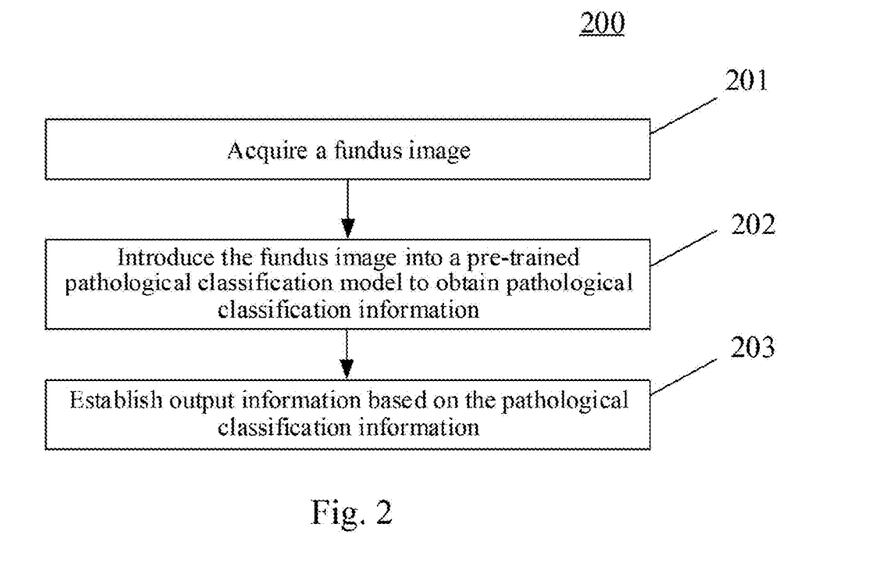
FIG. 2 is a flowchart of an embodiment of a method for acquiring information according to the present disclosure.

By further referring to FIG. 2, a flow 200 of an embodiment of a method for acquiring information according to the present disclosure is shown. The method for acquiring information includes following steps:

Step 201: acquiring a fundus image.

In this embodiment, an electronic device (e.g., the server 105 as shown in FIG. 1) on which the method for acquiring information runs may acquire the fundus image from the terminal devices 101, 102 and 103 by way of wired connection or wireless connection. It should be noted that the wireless connection may include, but is not limited to, 3G/4G connection, WiFi connection, Bluetooth connection, WiMAX connection, Zigbee connection, UWB (ultra wideband) connection, and other wireless connections that are known at present or are to be developed in the future.

Usually, fundus images may be directly acquired by a terminal device (e.g., a digital fundus camera) and sent to the server 105, or may also be indirectly acquired by a terminal device from other devices, and then sent to the server 105. The fundus image contains possible diabetic retinopathy focus images and diabetic macular edema focus images.

Step 202: introducing the fundus image into a pre-trained pathological classification model to obtain pathological classification information.

After a fundus image is acquired, the fundus image may be introduced into a pre-trained pathological classification model. The pathological classification model is used for characterizing correspondence between a pathological area image contained from the fundus image and the pathological classification information. With the pathological classification model, the pathological classification information corresponding to the fundus image may be obtained. When the fundus image contains at least one of a pathological area image of diabetic retinopathy and a pathological area image of diabetic macular edema, the obtained pathological classification information includes at least one of the diabetic retinopathy classification information and the diabetic macular edema classification information. The diabetic retinopathy classification information may include 1 to 5 levels; and the diabetic macular edema classification information may include 1 to 4 levels. When the classification information is 1, the fundus image may be considered as excluding diabetic retinopathy or diabetic macular edema.

In some optional implementations of the embodiment, the method according to the embodiment may further include establishing a pathological classification model, and the establishing a pathological classification model may include following steps:

Step I: retrieving a reference fundus image from a fundus image database.

The fundus image database contains a considerable amount of annotated fundus images. To train the pathological classification model, the annotated fundus images may be pre-retrieved from a fundus image database. The annotated fundus image contains a diabetic retinopathy area image and a diabetic macular edema area image, and is annotated with the diabetic retinopathy classification information and the diabetic macular edema classification information.

Step II: determining a first information block, and a second information block corresponding to the first information block from the annotated fundus image to obtain a first information block set and a second information block set corresponding to the fundus image database.

In order to be able to concurrently identify diabetic retinopathy and diabetic macular edema, the annotated fundus image according to the embodiment may contain both a diabetic retinopathy area image and a diabetic macular edema area image, to retain the information of correlation between diabetic retinopathy and diabetic macular edema. Each reference fundus image contains a diabetic retinopathy area image and a diabetic macular edema area image, and contains diabetic retinopathy classification information and diabetic macular edema classification information. Moreover, there is correlation between diabetic retinopathy and diabetic macular edema. Therefore, a first information block and a second information block corresponding to the first information block of each reference fundus image may be established. The first information block is used for characterizing correspondence between the diabetic retinopathy area image and the diabetic retinopathy classification information, and the second information block is used for characterizing correspondence between the diabetic macular edema area image and the diabetic macular edema classification information. There is correspondence between the first information block and the second information block of a given reference fundus image. The correspondence is used for reflecting the correlation between diabetic retinopathy and diabetic macular edema. Then a first information block set and a second information block set corresponding to the fundus image database may be obtained.

Step III: obtaining a pathological classification model by training, using a machine learning method based on the first information block set and the second information block set.

The server 105 may obtain a pathological classification model by training, using a machine learning method, respectively with the first information block set and the second information block set as inputs, and respectively with the diabetic retinopathy classification information and the diabetic macular edema classification information as outputs. Specifically, after the neural network model acquires characteristic information of diabetic retinopathy and diabetic macular edema, the server 105 may use models for classifying, such as Naive Bayesian Model (NBM) or Support Vector Machine (SVM), with the diabetic retinopathy area image as model input and the diabetic retinopathy classification information as corresponding model output, whilst with the diabetic macular edema area image as model input and the diabetic macular edema classification information as corresponding model output, by using a machine learning method, train the model to obtain a pathological classification model.

In some optional implementations of the embodiment, the obtaining a pathological classification model by training, using a machine learning method based on the first information block set and the second information block set may include following steps:

Step I: introducing the first information block and the second information block set corresponding to the first information block into a neural network to obtain a first feedback parameter corresponding to the first information block and a second feedback parameter corresponding to the second information block.

In the process of training the pathological classification model, the situations frequently arise that the diabetic retinopathy focus image does not accurately match with the diabetic retinopathy classification information, or the diabetic macular edema focus image does not accurately match with the diabetic macular edema classification information. Under the circumstance, it is necessary to adjust a plurality of parameters of the neural network. According to the present disclosure, the neural network is adjusted based on the first feedback parameter and the second feedback parameter. The first feedback parameter is used for characterizing the accuracy in acquiring the diabetic retinopathy classification information by the neural network. For example, when the diabetic macular edema classification information corresponding to the diabetic macular edema focus image should be level 2, while the diabetic macular edema classification information obtained by the neural network should be level 1, the first feedback parameter may be set as +25%; while the diabetic macular edema classification information obtained by the neural network should be level 3, the first feedback parameter may be set as −25%. The second feedback parameter is used for characterizing the accuracy in acquiring the diabetic macular edema classification information by the neural network. The value of the second feedback parameter is similar to the value of the first feedback parameter. It should be noted that, based on the actual needs of the neural network, the first feedback parameter and the second feedback parameter may have a plurality of value forms, including not only the percentage forms, but also other qualitative descriptions (for example, when the neural network is a fuzzy neural network, the first feedback parameter and the second feedback parameter may be: increase or decrease), specifically depending on actual needs.

Step II: correcting network parameters of the neural network based on the first feedback parameter and the second feedback parameter, and using the neural network with the corrected network parameters as the pathological classification model.

In practice, it usually needs to correct network parameters of the neural network multiple times based on the first feedback parameter and the second feedback parameter. When the output result reaches a certain accuracy degree, network parameters of the neural network may be fixed, i.e., here the correction on the network parameters is completed. The neural network with the corrected network parameters may be used as the pathological classification model.

In some optional implementations of the embodiment, the neural network according to the present disclosure may include: a convolutional layer and a fully connected layer, wherein the convolutional layer is used for processing the fundus image, and extracting characteristic information existing in a diabetic retinopathy area and a diabetic macular edema area of the fundus image, and the fully connected layer is used for respectively establishing first correspondence between image processing results of the diabetic retinopathy focus area and the diabetic retinopathy classification information, and establishing second correspondence between image processing results of the diabetic macular edema focus area and the diabetic macular edema classification information.

In order to concurrently acquire the diabetic retinopathy classification information and the diabetic macular edema classification information from the fundus image, the neural network according to the present disclosure may include a plurality of convolutional layers, the diabetic retinopathy area image and the diabetic macular edema area image of the fundus image are simultaneously processed by the plurality of convolutional layers, and finally a fully connected layer respectively establishes first correspondence between image processing results of the diabetic retinopathy focus area and the diabetic retinopathy classification information, and establishes second correspondence between image processing results of the diabetic macular edema focus area and the diabetic macular edema classification information, so that the diabetic retinopathy classification information and the diabetic macular edema classification information are outputted on the prerequisite of inputting the fundus image containing the diabetic retinopathy area image and the diabetic macular edema area image.

In some optional implementations of the embodiment, the correcting network parameters of the neural network based on the first feedback parameter and the second feedback parameter may include: correcting network parameters of at least one of the convolutional layer and the fully connected layer based on the first feedback parameter and the second feedback parameter.

The above neural network includes the convolutional layer and the fully connected layer, and the convolutional layer can simultaneously perform image processing on the diabetic retinopathy focus image and the diabetic macular edema focus image contained from the fundus image. In order to explore the correlation between diabetic retinopathy and diabetic macular edema, network parameters of at least one of the convolutional layer and the fully connected layer may be corrected based on the first feedback parameter and the second feedback parameter, so as to reflect the correlation between diabetic retinopathy and diabetic macular edema, and achieve simultaneous improvement on the accuracy of the diabetic retinopathy classification information and the diabetic macular edema classification information.

In some optional implementations of the embodiment, the neural network according to the present disclosure may include: a first hierarchical network and a second hierarchical network, wherein the first hierarchical network is used for establishing correspondence between the diabetic retinopathy focus area and the diabetic retinopathy classification information, and the second hierarchical network is used for establishing correspondence between the diabetic macular edema focus area and the diabetic macular edema classification information.

The diabetic retinopathy area image and the diabetic macular edema area image from the fundus image may not only be simultaneously processed by the convolution layer, but may also be respectively processed by the first hierarchical network and the second hierarchical network. The first hierarchical network and the second hierarchical network may each contain the neural network structures, such as the convolutional layer and the fully connected layer. The first hierarchical network is used for establishing correspondence between the diabetic retinopathy area image and the diabetic retinopathy classification information, and outputting the diabetic retinopathy classification information when a fundus image containing the diabetic retinopathy area image is input. The second hierarchical network is used for establishing correspondence between the diabetic macular edema area image and the diabetic macular edema classification information, and outputting the diabetic macular edema classification information when a fundus image containing the diabetic macular edema area image is input.

In some optional implementations of the embodiment, the correcting network parameters of the neural network based on the first feedback parameter and the second feedback parameter may include: correcting network parameters of the second hierarchical network based on the first feedback parameter, and correcting network parameters of the first hierarchical network based on the second feedback parameter.

When the neural network respectively obtains the diabetic retinopathy classification information and the diabetic macular edema classification information based on the first hierarchical network and the second hierarchical network, network parameters of the second hierarchical network may be corrected based on the first feedback parameter, and network parameters of the first hierarchical network may be corrected based on the second feedback parameter, so as to explore the correlation between diabetic retinopathy and diabetic macular edema. It should be noted that here, some of network parameters of the second hierarchical network are corrected based on the first feedback parameter. Likewise, some of network parameters of the first hierarchical network are corrected based on the second feedback parameter.

It should be noted that the pathological classification model may be trained by using a deep learning algorithm or other existing algorithm or an algorithm that is likely to arise in the future. The algorithm for training the pathological classification model is not limited to the embodiment.

Step 203: establishing output information based on the pathological classification information.

After acquiring the pathological classification information, output information may be established based on the pathological classification information as required.

Figure 3:
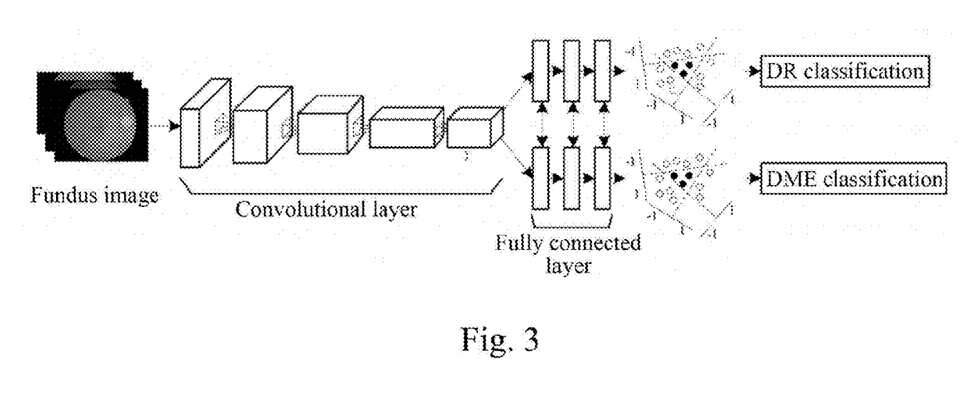
FIG. 3 is a schematic diagram of an application scenario of a method for acquiring information according to the present disclosure.

Further referring to FIG. 3, FIG. 3 is a schematic diagram of an application scenario of a method for acquiring information according to the embodiment. In the application scenario of FIG. 3, the acquired fundus image contains the diabetic retinopathy focus image (e.g., venous rings in FIG. 3) and the diabetic macular edema focus image (e.g., cotton-wool spots in FIG. 3). The diabetic retinopathy classification information and the diabetic macular edema classification information are obtained by inputting the fundus image into the pathological classification model. Then output information is established based on the diabetic retinopathy classification information and the diabetic macular edema classification information.

The method provided in the embodiments of the present disclosure may concurrently acquire diabetic retinopathy classification information and diabetic macular edema classification information from the fundus image, and may make full use of the correlation between diabetic retinopathy and diabetic macular edema in diagnosis to effectively improve the accuracy of diabetic retinopathy classification and diabetic macular edema classification in the process of computer aided diagnosis.

Figure 4:
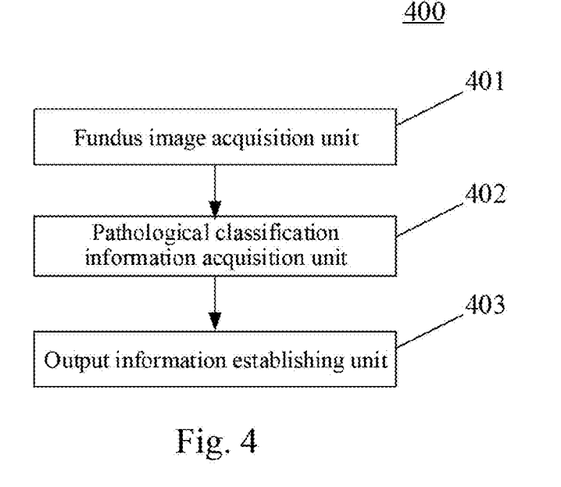
FIG. 4 is a structural schematic diagram of an embodiment of an apparatus for acquiring information according to the present disclosure.

Further referring to FIG. 4, as implementations of the methods shown in the figures, the present disclosure provides an embodiment of an apparatus for acquiring information. The embodiment of the apparatus corresponds to the embodiment of the method shown in FIG. 2, and the apparatus may be applied to a variety of electronic devices.

As shown in FIG. 4, the apparatus 400 for acquiring information according to the embodiment may include: a fundus image acquisition unit 401, a pathological classification information acquisition unit 402 and an output information establishing unit 403. The fundus image acquisition unit 401 is used for acquiring a fundus image; and the pathological classification information acquisition unit 402 is used for introducing the fundus image into a pre-trained pathological classification model to obtain pathological classification information, wherein the pathological classification model is used for characterizing correspondence between a pathological area image contained from the fundus image and the pathological classification information, and the pathological classification information includes at least one of diabetic retinopathy classification information and diabetic macular edema classification information; and the output information establishing unit 403 is used for establishing output information based on the pathological classification information.

In some optional implementations of the embodiment, the apparatus further includes a pathological classification model establishing unit (not shown in the figure) for establishing a pathological classification model. The pathological classification model establishing unit may include an annotated fundus image retrieval subunit (not shown in the figure), an information block set acquisition subunit (not shown in the figure) and a pathological classification model training subunit (not shown in the figure). The annotated fundus image retrieval subunit is used for retrieving an annotated fundus image from a fundus image database, wherein the annotated fundus image includes a diabetic retinopathy area image and a diabetic macular edema area image, as well as the diabetic retinopathy classification information and the diabetic macular edema classification information; an information block set acquisition subunit is used for determining a first information block, and a second information block corresponding to the first information block from the annotated fundus image to obtain a first information block set and a second information block set corresponding to the fundus image database, wherein the first information block is used for characterizing correspondence between the diabetic retinopathy area image and the diabetic retinopathy classification information, and the second information block is used for characterizing correspondence between the diabetic macular edema area image and the diabetic macular edema classification information; and the pathological classification model training subunit is used for obtaining a pathological classification model by training, using a machine learning method based on the first information block set and the second information block set.

In some optional implementations of the embodiment, the pathological classification model training subunit may include: a feedback parameter acquisition module (not shown in the figure) and a pathological classification model acquisition module (not shown in the figure). The feedback parameter acquisition module is used for introducing the first information block and the second information block set corresponding to the first information block into a neural network to obtain a first feedback parameter corresponding to the first information block and a second feedback parameter corresponding to the second information block, wherein the first feedback parameter is used for characterizing the accuracy in acquiring the diabetic retinopathy classification information by the neural network, and the second feedback parameter is used for characterizing the accuracy in acquiring the diabetic macular edema classification information by the neural network; and the pathological classification model acquisition module is used for correcting network parameters of the neural network based on the first feedback parameter and the second feedback parameter, and using the neural network with the corrected network parameters as the pathological classification model.

In some optional implementations of the embodiment, the neural network may include: a convolutional layer and a fully connected layer, wherein the convolutional layer is used for processing the fundus image, and extracting characteristic information existing in a diabetic retinopathy area and a diabetic macular edema area of the fundus image, and the fully connected layer is used for respectively establishing first correspondence between image processing results of the diabetic retinopathy focus area and the diabetic retinopathy classification information, and establishing second correspondence between image processing results of the diabetic macular edema focus area and the diabetic macular edema classification information.

In some optional implementations of the embodiment, the pathological classification model acquisition module may include: correcting network parameters of at least one of the convolutional layer and the fully connected layer based on the first feedback parameter and the second feedback parameter.

In some optional implementations of the embodiment, the neural network may include: a first hierarchical network and a second hierarchical network, wherein the first hierarchical network is used for establishing correspondence between the diabetic retinopathy focus area and the diabetic retinopathy classification information, and the second hierarchical network is used for establishing correspondence between the diabetic macular edema focus area and the diabetic macular edema classification information.

In some optional implementations of the embodiment, the pathological classification model acquisition module may include: correcting network parameters of the second hierarchical network based on the first feedback parameter, and correcting network parameters of the first hierarchical network based on the second feedback parameter.

The embodiment further provides a server, including: one or more processors; and a memory, for storing one or more programs, wherein the one or more programs enable, when executed by the one or more processors, the one or more processors to execute the above method for acquiring information.

The embodiment further provides a computer readable storage medium storing a computer program therein, wherein the program implements, when executed by a processor, the above method for acquiring information.

Figure 5:
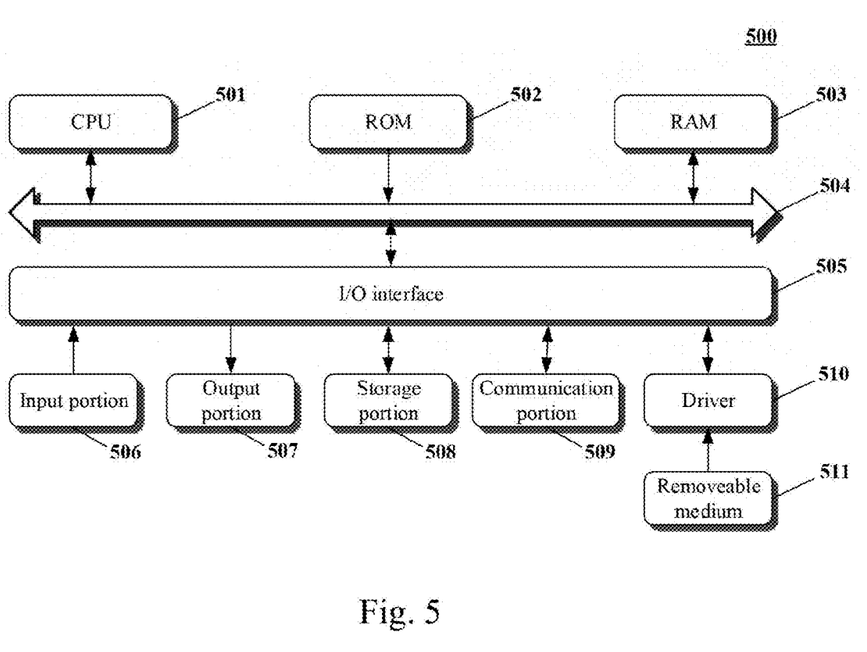
FIG. 5 is a structural schematic diagram of a computer system suitable for implementing the server according to an embodiment of the present disclosure.

Referring to FIG. 5, a schematic structural diagram of a computer system 500 adapted to implement a server of the embodiments of the present disclosure is shown. The server shown in FIG. 5 is only an example, and should not impose any limitation on the function and the usage range of the embodiments of the present disclosure.

As shown in FIG. 5, the computer system 500 includes a central processing unit (CPU) 501, which may execute various appropriate actions and processes in accordance with a program stored in a read-only memory (ROM) 502 or a program loaded into a random access memory (RAM) 503 from a storage portion 508. The RAM 503 also stores various programs and data required by operations of the system 500. The CPU 501, the ROM 502 and the RAM 503 are connected to each other through a bus 504. An input/output (I/O) interface 505 is also connected to the bus 504.

The following components are connected to the I/O interface 505: an input portion 506 including a keyboard, a mouse etc.; an output portion 507 comprising a cathode ray tube (CRT), a liquid crystal display device (LCD), a speaker etc.; a storage portion 508 including a hard disk and the like; and a communication portion 509 comprising a network interface card, such as a LAN card and a modem. The communication portion 509 performs communication processes via a network, such as the Internet. A driver 510 is also connected to the I/O interface 505 as required. A removable medium 511, such as a magnetic disk, an optical disk, a magneto-optical disk, and a semiconductor memory, may be installed on the driver 510, to facilitate the retrieval of a computer program from the removable medium 511, and the installation thereof on the storage portion 508 as needed.

In particular, according to embodiments of the present disclosure, the process described above with reference to the flow chart may be implemented in a computer software program. For example, an embodiment of the present disclosure includes a computer program product, which comprises a computer program that is tangibly embedded in a machine-readable medium. The computer program comprises program codes for executing the method as illustrated in the flow chart. In such an embodiment, the computer program may be downloaded and installed from a network via the communication portion 509, and/or may be installed from the removable media 511. The computer program, when executed by the central processing unit (CPU) 501, implements the above mentioned functionalities as defined by the methods of the present disclosure.

It should be noted that the computer readable medium in the present disclosure may be computer readable signal medium or computer readable storage medium or any combination of the above two. An example of the computer readable storage medium may include, but not limited to: electric, magnetic, optical, electromagnetic, infrared, or semiconductor systems, apparatus, elements, or a combination any of the above. A more specific example of the computer readable storage medium may include but is not limited to: electrical connection with one or more wire, a portable computer disk, a hard disk, a random access memory (RAM), a read only memory (ROM), an erasable programmable read only memory (EPROM or flash memory), a fibre, a portable compact disk read only memory (CD-ROM), an optical memory, a magnet memory or any suitable combination of the above. In the present disclosure, the computer readable storage medium may be any physical medium containing or storing programs which can be used by a command execution system, apparatus or element or incorporated thereto. In the present disclosure, the computer readable signal medium may include data signal in the base band or propagating as parts of a carrier, in which computer readable program codes are carried. The propagating signal may take various forms, including but not limited to: an electromagnetic signal, an optical signal or any suitable combination of the above. The signal medium that can be read by computer may be any computer readable medium except for the computer readable storage medium. The computer readable medium is capable of transmitting, propagating or transferring programs for use by, or used in combination with, a command execution system, apparatus or element. The program codes contained on the computer readable medium may be transmitted with any suitable medium including but not limited to: wireless, wired, optical cable, RF medium etc., or any suitable combination of the abov The flow charts and block diagrams in the accompanying drawings illustrate architectures, functions and operations that may be implemented according to the systems, methods and computer program products of the various embodiments of the present disclosure. In this regard, each of the blocks in the flowcharts or block diagrams may represent a module, a program segment, or a code portion, said module, program segment, or code portion comprising one or more executable instructions for implementing specified logic functions. It should also be noted that, in some alternative implementations, the functions denoted by the blocks may occur in a sequence different from the sequences shown in the figures. For example, any two blocks presented in succession may be executed, substantially in parallel, or they may sometimes be in a reverse sequence, depending on the function involved. It should also be noted that each block in the block diagrams and/or flow charts as well as a combination of blocks may be implemented using a dedicated hardware-based system executing specified functions or operations, or by a combination of a dedicated hardware and computer instructions.

The units or modules involved in the embodiments of the present disclosure may be implemented by means of software or hardware. The described units or modules may also be provided in a processor, for example, described as: a processor, comprising a fundus image acquisition unit, a pathological classification information acquisition unit and an output information establishing unit, where the names of these units or modules do not in some cases constitute a limitation to such units or modules themselves. For example, the output information establishing unit may also be described as "a unit for establishing output information."

In another aspect, the present disclosure further provides a computer-readable storage medium. The computer-readable storage medium may be the computer storage medium included in the apparatus in the above described embodiments, or a stand-alone computer-readable storage medium not assembled into the apparatus. The computer-readable storage medium stores one or more programs. The one or more programs, when executed by a device, cause the device to: acquire a fundus image; introduce the fundus image into a pre-trained pathological classification model to obtain pathological classification information, wherein the pathological classification model is used for characterizing correspondence between a pathological area image contained from the fundus image and the pathological classification information, and the pathological classification information comprises at least one of diabetic retinopathy classification information and diabetic macular edema classification information; and establish output information based on the pathological classification information.

The above description only provides an explanation of the preferred embodiments of the present disclosure and the technical principles used. It should be appreciated by those skilled in the art that the inventive scope of the present disclosure is not limited to the technical solutions formed by the particular combinations of the above-described technical features. The inventive scope should also cover other technical solutions formed by any combinations of the above-described technical features or equivalent features thereof without departing from the concept of the present disclosure. Technical schemes formed by the above-described features being interchanged with, but not limited to, technical features with similar functions disclosed in the present disclosure are examples.

What is claimed is:
1. A method for acquiring information, comprising:
establishing a pathological classification model;
acquiring a fundus image;
introducing the fundus image into the pathological classification model to obtain pathological classification information, wherein the pathological classification model is used for characterizing correspondence between a pathological area image contained from the fundus image and the pathological classification information, and the pathological classification information comprises at least one of diabetic retinopathy classification information and diabetic macular edema classification information; and
establishing output information based on the pathological classification information,
wherein the establishing a pathological classification model comprises:
retrieving an annotated fundus image from a fundus image database, wherein the annotated fundus image comprises a diabetic retinopathy area image and a diabetic macular edema area image, as well as the diabetic retinopathy classification information and the diabetic macular edema classification information;
determining a first information block, and a second information block corresponding to the first information block from the annotated fundus image to obtain a first information block set and a second information block set corresponding to the fundus image database, wherein the first information block is used for characterizing correspondence between the diabetic retinopathy area image and the diabetic retinopathy classification information, and the second information block is used for characterizing correspondence between the diabetic macular edema area image and the diabetic macular edema classification information; and
obtaining a pathological classification model by training, using a machine learning method based on the first information block set and the second information block set.

2. The method according to claim 1, wherein the obtaining a pathological classification model by training, using a machine learning method based on the first information block set and the second information block set comprises:

introducing the first information block and the second information block set corresponding to the first information block into a neural network to obtain a first feedback parameter corresponding to the first information block and a second feedback parameter corresponding to the second information block, wherein the first feedback parameter is used for characterizing the accuracy in acquiring the diabetic retinopathy classification information by the neural network, and the second feedback parameter is used for characterizing the accuracy in acquiring the diabetic macular edema classification information by the neural network; and correcting network parameters of the neural network based on the first feedback parameter and the second feedback parameter, and using the neural network with the corrected network parameters as the pathological classification model.

3. The method according to claim 2, wherein the neural network comprises:

a convolutional layer and a fully connected layer, wherein the convolutional layer is used for processing the fundus image, and extracting characteristic information existing in a diabetic retinopathy area and a diabetic macular edema area of the fundus image, and the fully connected layer is used for respectively establishing first correspondence between image processing results of the diabetic retinopathy focus area and the diabetic retinopathy classification information, and establishing second correspondence between image processing results of the diabetic macular edema focus area and the diabetic macular edema classification information.

4. The method according to claim 3, wherein the correcting network parameters of the neural network based on the first feedback parameter and the second feedback parameter comprises:

correcting network parameters of at least one of the convolutional layer and the fully connected layer based on the first feedback parameter and the second feedback parameter.

5. The method according to claim 2, wherein the neural network comprises:

a first hierarchical network and a second hierarchical network, wherein the first hierarchical network is used for establishing correspondence between the diabetic retinopathy focus area and the diabetic retinopathy classification information, and the second hierarchical network is used for establishing correspondence between the diabetic macular edema focus area and the diabetic macular edema classification information.

6. The method according to claim 5, wherein the correcting network parameters of the neural network based on the first feedback parameter and the second feedback parameter comprises:

correcting network parameters of the second hierarchical network based on the first feedback parameter, and correcting network parameters of the first hierarchical network based on the second feedback parameter.

7. An apparatus for acquiring information, comprising:
at least one processor; and
a memory storing instructions, the instructions when executed by the at least one processor, cause the at least one processor to perform operations, the operations comprising:

establishing a pathological classification model;
acquiring a fundus image;
introducing the fundus image into the pathological classification model to obtain pathological classification information, wherein the pathological classification model is used for characterizing correspondence between a pathological area image contained from the fundus image and the pathological classification information, and the pathological classification information comprises at least one of diabetic retinopathy classification information and diabetic macular edema classification information; and establishing output information based on the pathological classification information, wherein the establishing a pathological classification model comprises:

retrieving an annotated fundus image from a fundus image database, wherein the annotated fundus image comprises a diabetic retinopathy area image and a diabetic macular edema area image, as well as the diabetic retinopathy classification information and the diabetic macular edema classification information;

determining a first information block, and a second information block corresponding to the first information block from the annotated fundus image to obtain a first information block set and a second information block set corresponding to the fundus image database, wherein the first information block is used for characterizing correspondence between the diabetic retinopathy area image and the diabetic retinopathy classification information, and the second information block is used for characterizing correspondence between the diabetic macular edema area image and the diabetic macular edema classification information; and obtaining a pathological classification model by training, using a machine learning method based on the first information block set and the second information block set.

8. The apparatus according to claim 7, wherein the obtaining a pathological classification model by training, using a machine learning method based on the first information block set and the second information block set comprises:

introducing the first information block and the second information block set corresponding to the first information block into a neural network to obtain a first feedback parameter corresponding to the first information block and a second feedback parameter corresponding to the second information block, wherein the first feedback parameter is used for characterizing the accuracy in acquiring the diabetic retinopathy classification information by the neural network, and the second feedback parameter is used for characterizing the accuracy in acquiring the diabetic macular edema classification information by the neural network; and correcting network parameters of the neural network based on the first feedback parameter and the second feedback parameter, and using the neural network with the corrected network parameters as the pathological classification model.

9. The apparatus according to claim 8, wherein the neural network comprises:

a convolutional layer and a fully connected layer, wherein the convolutional layer is used for processing the fundus image, and extracting characteristic information existing in a diabetic retinopathy area and a diabetic macular edema area of the fundus image, and the fully connected layer is used for respectively establishing first correspondence between image processing results of the diabetic retinopathy focus area and the diabetic retinopathy classification information, and establishing second correspondence between image processing results of the diabetic macular edema focus area and the diabetic macular edema classification information.

10. The apparatus according to claim 9, wherein the correcting network parameters of the neural network based on the first feedback parameter and the second feedback parameter comprises:
correcting network parameters of at least one of the convolutional layer and the fully connected layer based on the first feedback parameter and the second feedback parameter.

11. The apparatus according to claim 8, wherein the neural network comprises:
a first hierarchical network and a second hierarchical network, wherein the first hierarchical network is used for establishing correspondence between the diabetic retinopathy focus area and the diabetic retinopathy classification information, and the second hierarchical network is used for establishing correspondence between the diabetic macular edema focus area and the diabetic macular edema classification information.

12. The apparatus according to claim 11, wherein the correcting network parameters of the neural network based on the first feedback parameter and the second feedback parameter comprises:
correcting network parameters of the second hierarchical network based on the first feedback parameter, and correcting network parameters of the first hierarchical network based on the second feedback parameter.

13. A non-transitory computer readable storage medium, storing a computer program thereon, wherein the computer program, when executed by a processor, cause the processor to perform operations, the operations comprise:
establishing a pathological classification model;
acquiring a fundus image;
introducing the fundus image into the pathological classification model to obtain pathological classification information, wherein the pathological classification model is used for characterizing correspondence between a pathological area image contained from the fundus image and the pathological classification information, and the pathological classification information comprises at least one of diabetic retinopathy classification information and diabetic macular edema classification information; and
establishing output information based on the pathological classification information,
wherein the establishing a pathological classification model comprises:
retrieving an annotated fundus image from a fundus image database, wherein the annotated fundus image comprises a diabetic retinopathy area image and a diabetic macular edema area image, as well as the diabetic retinopathy classification information and the diabetic macular edema classification information;
determining a first information block, and a second information block corresponding to the first information block from the annotated fundus image to obtain a first information block set and a second information block set corresponding to the fundus image database, wherein the first information block is used for characterizing correspondence between the diabetic retinopathy area image and the diabetic retinopathy classification information, and the second information block is used for characterizing correspondence between the diabetic macular edema area image and the diabetic macular edema classification information; and
obtaining a pathological classification model by training, using a machine learning method based on the first information block set and the second information block set.

* * * * *